(12) United States Patent
Marteau et al.

(10) Patent No.: US 6,692,463 B1
(45) Date of Patent: Feb. 17, 2004

(54) SYRINGE HOLDER

(75) Inventors: Denis Marteau, Oxford (GB); Glenn Davison, Oxon (GB)

(73) Assignee: Owen Mumford Limited, Oxford (GB)

( * ) Notice: Subject to any disclaimer, the term of this patent is extended or adjusted under 35 U.S.C. 154(b) by 83 days.

(21) Appl. No.: 09/703,797

(22) Filed: Nov. 2, 2000

(30) Foreign Application Priority Data

Nov. 2, 1999 (GB) ............................... 9925820

(51) Int. Cl.[7] .............................. A61M 5/00; A61M 5/32
(52) U.S. Cl. ...................... 604/110; 604/195; 604/192; 604/232; 604/187
(58) Field of Search ................................ 604/187, 232, 604/208, 110, 195–192, 193, 198; 128/919

(56) References Cited

U.S. PATENT DOCUMENTS

| | | | |
|---|---|---|---|
| 563,222 A | * 6/1896 | Mahurka | 366/327.2 |
| 4,540,405 A | 9/1985 | Miller et al. | |
| 5,088,986 A | 2/1992 | Nusbaum | |
| 5,643,222 A | * 7/1997 | Mahurkar | 604/195 |
| 5,893,842 A | * 4/1999 | Imbert | 604/110 |
| 5,997,513 A | * 12/1999 | Smith et al. | 128/919 |

FOREIGN PATENT DOCUMENTS

| | | |
|---|---|---|
| EP | 0 845 275 A2 | 6/1998 |
| WO | 94/13347 | 6/1994 |

OTHER PUBLICATIONS

Verdine et al, Drug Delivery system including holder and drug container, Publication date Jan. 24, 02, U.S. patent application Publication, Publication No. U.S. 2002/0010428 A1.*

* cited by examiner

*Primary Examiner*—Manuel Mendez
*Assistant Examiner*—Roz Ghafoorian
(74) *Attorney, Agent, or Firm*—Young & Thompson

(57) ABSTRACT

A syringe holder has a barrel (1) with a sleeve (2) screwed over its forward end. A syringe is entered into the rear end of the barrel (1), needle (20) first, with the sleeve (2) at its rearmost position. A coned needle cap (23) snaps through an aperture (13) at the forward end of the sleeve as a flange (18) at the rear of the syringe tube (17) abuts the rear end of the barrel (1). Screwing the sleeve (2) forwards eases the cap (23) off the needle (20), and screwing it back again leaves the assembly ready to use. The barrel (1) has finger grips (10) to facilitate thumb operation of the syringe plunger.

8 Claims, 2 Drawing Sheets

SYRINGE HOLDER

BACKGROUND OF THE INVENTION

This invention relates to a syringe holder.

DESCRIPTION OF THE RELATED ART

A common, simple syringe consists of a glass tube with a needle projecting from its forward end, and an out-turned flange at its open, rear end. The dose is trapped and ejected through the needle by a plunger entered through this rear end. At manufacture, and until just before use, the needle is encased in a shroud to keep it sterile, and to prevent accidental pricking. Such a syringe will be referred to as of the kind described.

These syringes may be used on their own, but their small size and the slipperiness of the glass tube make them difficult to handle, particularly for self-users such as sufferers from rheumatoid arthritis.

There are various firing devices into which such a syringe can be inserted, these generally having the appearance of a fountain pen. These are larger and easier to handle, and the actual injection may be carried out by a spring mechanism released by a trigger. Often, these pen-like devices have a cap arrangement which, when removed just before use, takes with it the needle shroud.

However, such elaboration is not always required, and there is believed to be a demand for something that will make handling the basic syringe easier and the removal of the needle shroud simple and safe. This invention is aimed at that.

SUMMARY OF THE INVENTION

According to the present invention there is provided a syringe holder comprising a barrel to receive a syringe of the kind described through its open rear end, against whose rim the outwardly projecting flange at the rear of the syringe will abut when the syringe is fully inserted, and a sleeve screw threaded onto the forward end of the barrel with an inturned flange at its own forward end forming an aperture through which a needle cap on a syringe can snap when the syringe is fully inserted and when the sleeve is screwed to its rearmost position, screwing the sleeve forward from that position causing the flange to ease the cap off the syringe needle.

Once the needle cap has been removed, the sleeve is screwed back again fully to expose the needle and the syringe is ready for injection.

Conveniently, the barrel will have opposed wings rearwardly of the sleeve to afford a finger grip so that the user holds the assembly there and then pushes on the plunger.

The rear end of the barrel may have two opposed cut away portions leaving the rim at the rear of the barrel with two arcuate sections on which the syringe flange will bear. This makes the syringe easier to grip and remove after use.

Preferably, the sleeve will be captive to the barrel. This can be achieved by the sleeve having angled slots into which projecting studs on the barrel can snap on assembly, these slots and studs also forming the screw-threaded engagement.

Further, lesser projecting studs may be provided on the barrel and be arranged to snap into the rear ends of the slots when the sleeve is in its rearmost position. Thus the retracted sleeve is lightly held and will require positive manipulation, to move it forwards.

BRIEF DESCRIPTION OF THE DRAWINGS

For a better understanding of the invention, one embodiment will now be described, by way of example, with reference to the accompanying drawing, in which.

DESCRIPTION OF THE PREFERRED EMBODIMENTS

Figure 1:
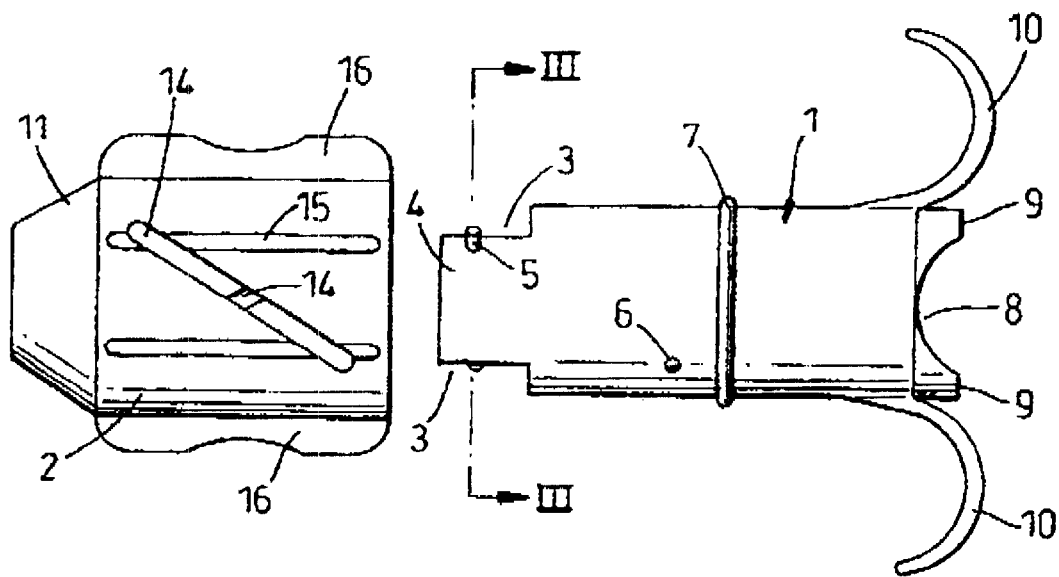
FIG. 1 is an exploded side view of a syringe holder.
Figure 2:
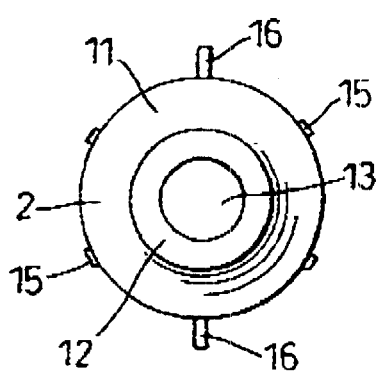
FIG. 2 is a forward end view of a sleeve forming part of the holder of FIG. 1.
Figure 3:
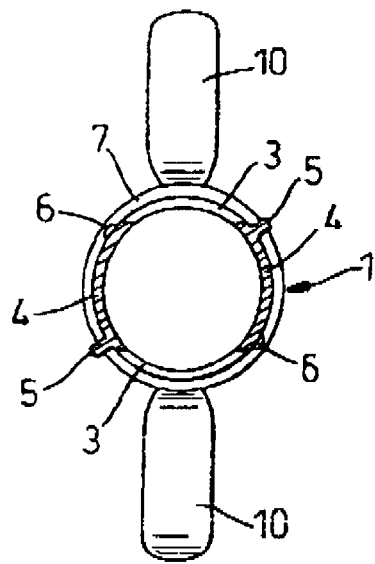
FIG. 3 is a cross-section on the line III—III of FIG. 1.

The syringe holder has a cylindrical barrel 1 open at both ends and a sleeve 2 which fits over the forward end of the barrel. At its forward end (to the left in FIG. 1) the barrel has two opposed axially parallel slots 3 open at their forward ends to form tongues 4 on which there are diametrically opposed radially projecting studs 5. Further to the rear there are two diametrically opposed pimples 6 circumferentially offset from the studs 5. A bit further back there is an annular rib 7, and at the rear end there are opposed half moon cutouts 8 leaving short arcuate sections 9 of what would otherwise be a circular rim. Springing out from the barrel 1 from just in front of these sections 9 are two curved wings 10 affording finger grips.

The sleeve 2 fits over the forward end of the barrel 1. It has a coned nose 11 with an inturned annular flange 12 leaving a circular aperture 13. In its main cylindrical part there are two opposed, angled, closed-end slots 14, and the tongues 4 are sufficiently resilient for the studs 5 to be forced into the rear end of the sleeve before snapping out into the slots 14. There is then a coarse screw-thread relationship between the sleeve 2 and the barrel 1, the studs 5 following the slots as the sleeve is moved back and forth on the barrel. When the studs 5 are at the forward ends of the slots 14, the pimples 6 snap into the rear ends of the slots and the rear end of the sleeve abuts the rib 7. The lesser height of the pimples 6 means that they only lightly impede the final rearward motion of the sleeve as they enter the sleeve, but that height is just sufficient for there to be positive engagement with the rear ends of the slots 14, which stops the sleeve 2 moving forwards again unless manually urged.

The main cylindrical part of the sleeve 2 has external longitudinally extending ribs 15 and wings 16 to afford a good grip.

Referring to FIG. 4, a syringe has a glass tube 17 with an outward flange 18 at its rear end and a neck 19 with a projecting needle 20 at its forward end. A plunger comprises a piston 21 slidable in the tube 17 and operated by a rod 22. Initially, the needle 20 is protected by a rubber or plastics cap, 23 which is generally frusto-conical with a very small apex angle, the wider end being to the rear. The smaller end will penetrate the aperture 13 when the syringe is entered through the barrel 1 from the rear. As it is pushed right home, the rear end of the cap is constricted by and then snaps through the aperture.

Figure 4A:
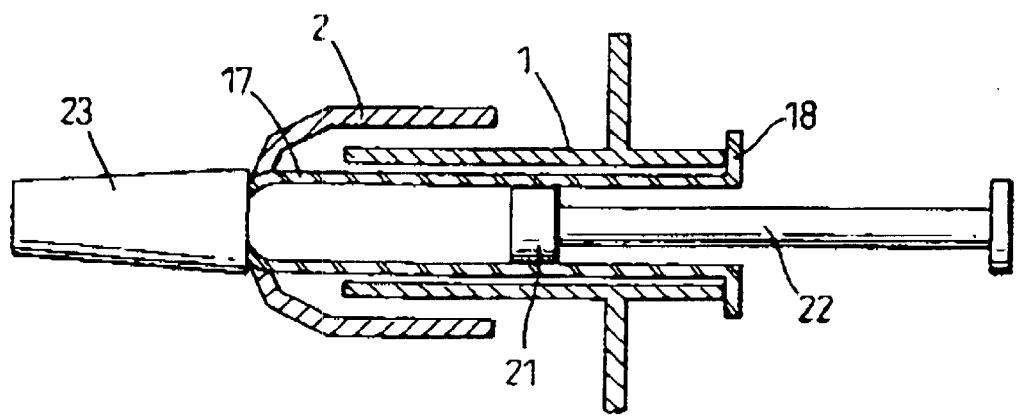
FIG. 4 shows the holder in simplified diagrammatic axial section with a syringe fitted, in three stages before and after injection.
Figure 4B:
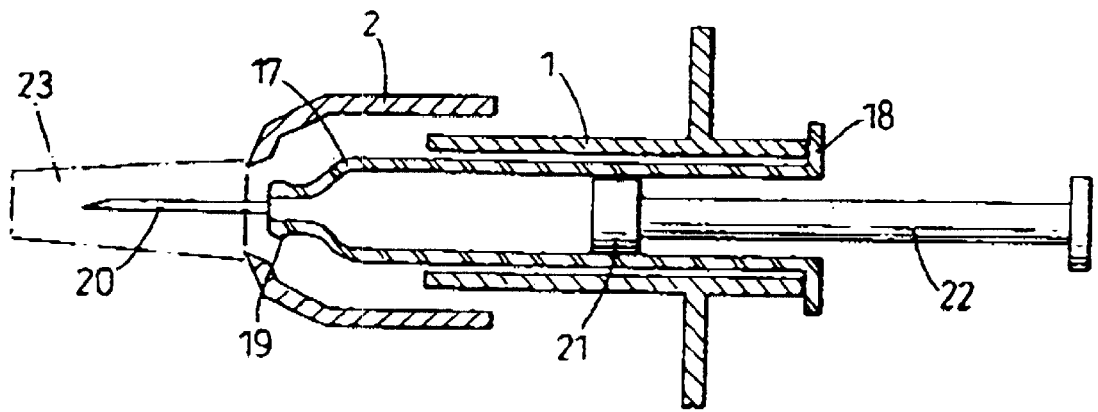
Figure 4C:
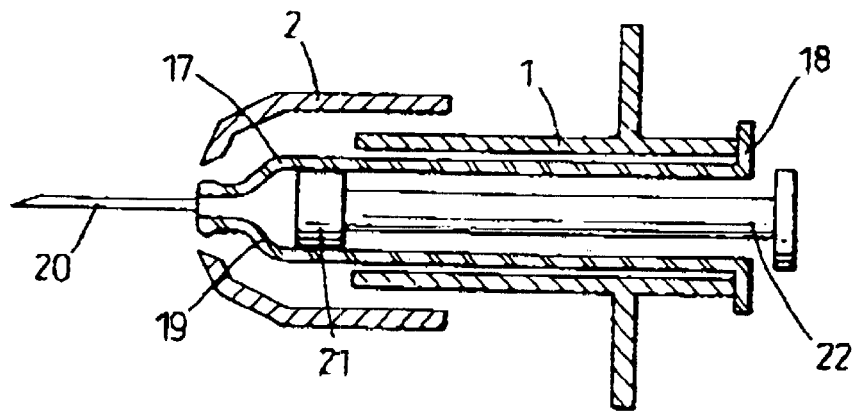

This is done with the sleeve 2 in its rearmost position (FIG. 4a). For use, the sleeve is screwed forwardly, and the flange 12 will ease the cap 23 off. By the time the sleeve is fully forward the cap will be loose enough just to be lifted clear without any exertion of force (FIG. 4b). The syringe is of course prevented from moving bodily forward by the engagement of the flange 18 with the rim sections 9.

The sleeve 2 is then screwed back to its initial position and the syringe can be used. It remains in the holder, with the user crooking two fingers under respective wings 10 and pressing the rear end of the plunger with the thumb.

After use (FIG. 4c), the syringe can be removed from the holder by gripping its flange 18 (which is facilitated by the cutouts 8) and pulling.

We claim:

1. A syringe holder for receiving in use a syringe type having
   a tube containing a substance to be administered,
   a needle projecting from a forward end of said tube,
   an outwardly projecting flange at a rearward end of said syringe, and
   a needle cap releasably attached to said syringe and enclosing said needle, said needle cap having a generally rearwardly facing external surface portion,
   said syringe holder comprising:
      a barrel having an open rear end through which open rear end said syringe may in use be received, and which defines a rim against which rim the outwardly projecting flange of the syringe abuts in use when the syringe is fully inserted;
      a sleeve screw-threaded onto a forward end of the barrel with an inturned flange at its own forward end forming an aperture through which said needle cap can snap in use to leave the rearwardly facing external surface portion of said needle cap disposed forwardly of said sleeve aperture when said syringe is fully inserted,
      wherein, when the sleeve is in its rearmost screwed position relative to said barrel, screwing the sleeve forwardly from that position causes the sleeve to ease the needle cap off said syringe.

2. A syringe holder as claimed in claim 1, further comprising a plunger;
   opposed wings located rearwardly of the sleeve on the barrel and providing a finger grip to a user holding the syringe holder at the finger grip and pushing on the plunger.

3. A syringe holder as claimed in claim 1, wherein the rear end of the barrel has two opposed cut away portions leaving the rim at the rear of the barrel with two arcuate sections on which the syringe flange will bear.

4. A syringe holder as claimed in claim 1, wherein the sleeve is captive to the barrel.

5. A syringe holder as claimed in claim 4, further comprising:
   angled slots on the sleeve;
   projecting studs on the barrel snapped into the angled slots on the sleeve,
   the slots and studs screw-threadedly engaging the sleeve to the barrel to render the sleeve captive to the barrel.

6. A syringe holder as claimed in claim 5, further comprising:
   further studs on the barrel, the further studs projecting less than the projecting studs and arranged to snap into rear ends of the angled slots when the sleeve is in its rearmost position.

7. A syringe assembly comprising, in combination:
   a syringe; and
   a syringe holder,
   said syringe comprising
      a tube containing a substance to be administered;
      a needle projecting from a forward end of said tube assembly;
      an outwardly projecting flange at a rearward end of said syringe, and
      a needle cap releasably attached to said syringe and enclosing said needle, said needle cap having a generally rearwardly facing external surface portion, and
   said syringe holder comprising
      a barrel having an open rear end through which open rear end the syringe is received and which defines a rim against which rim the outwardly projecting flange of the syringe abuts when the syringe is fully inserted,
      a sleeve screw-threaded onto a forward end of the barrel with an inturned flange at its own forward end forming an aperture through which said needle cap is snapped to leave the rearwardly facing external surface portion of said needle cap disposed forwardly of said sleeve aperture when said syringe is fully inserted in said syringe holder,
      wherein, when the sleeve is in its rearmost screwed position relative to said barrel, screwing the sleeve forwardly from that position causes the sleeve to ease the needle cap off said syringe.

8. A method of operating a syringe of the type having a tube containing a substance to be administered, a needle projecting from a forward end of the tube, an outwardly projecting flange at a rearward end of the syringe, and a needle cap releasably attached to the syringe and enclosing the needle, the needle cap having a generally rearwardly facing external surface portion, the method comprising the steps of:
   inserting the syringe into a two-part syringe holder wherein a first part and a second part are in screw-threaded engagement for being urged apart when screwed in an appropriate direction,
   positioning the syringe so that the needle cap snaps through an aperture in the second part to leave the rearwardly aperture and so that the syringe tube is located against forward movement relative to the first part, and
   thereafter screwing the second part so as to move the second part forwardly relative to the first part and thereby ease the needle cap off the syringe.

* * * * *